(12) United States Patent
Schwirtz et al.

(10) Patent No.: US 10,780,233 B2
(45) Date of Patent: Sep. 22, 2020

(54) ACTIVATOR FOR AN AUTOINJECTOR

(71) Applicant: PHARMA CONSULT GES.M.B.H., Vienna (AT)

(72) Inventors: Andreas Schwirtz, Vienna (AT); Markus Csenar, Vienna (AT)

(73) Assignee: PHARMA CONSULT GES.M.B.H., Vienna (AT)

(*) Notice: Subject to any disclaimer, the term of this patent is extended or adjusted under 35 U.S.C. 154(b) by 0 days.

(21) Appl. No.: 16/156,389

(22) Filed: Oct. 10, 2018

(65) Prior Publication Data
US 2019/0038845 A1    Feb. 7, 2019

Related U.S. Application Data

(63) Continuation of application No. 14/900,923, filed as application No. PCT/AT2014/000117 on Jun. 5, 2014, now Pat. No. 10,105,499.

(30) Foreign Application Priority Data

Jun. 24, 2013 (AU) ................................ A 514/2013

(51) Int. Cl.
*A61M 5/20* (2006.01)
*A61M 5/32* (2006.01)

(52) U.S. Cl.
CPC ........ *A61M 5/3204* (2013.01); *A61M 5/2033* (2013.01); *A61M 2005/202* (2013.01); *A61M 2005/206* (2013.01); *A61M 2005/2073* (2013.01)

(58) Field of Classification Search
CPC .......... A61M 5/2033; A61M 2005/202; A61M 2005/206; A61M 2005/2073; A61M 5/3204
USPC ......................................................... 604/134
See application file for complete search history.

(56) References Cited

U.S. PATENT DOCUMENTS

| 5,599,309 | A  | * | 2/1997 | Marshall ............. | A61M 5/2033 604/117 |
| 6,743,203 | B1 | * | 6/2004 | Pickhard ............. | A61M 5/2033 604/139 |
| 2007/0073232 | A1 | * | 3/2007 | Pickhard ............. | A61M 5/2033 604/134 |
| 2008/0015520 | A1 |   | 1/2008 | Hommann et al. | |
| 2011/0125100 | A1 |   | 5/2011 | Schwirtz | |

(Continued)

FOREIGN PATENT DOCUMENTS

| WO | WO 2009/022132 A2 | 2/2009 |
| WO | WO 2009/147026 A1 | 12/2009 |

(Continued)

*Primary Examiner* — Jason E Flick
(74) *Attorney, Agent, or Firm* — Sterne, Kessler, Goldstein & Fox P.L.L.C.

(57) ABSTRACT

The invention relates to an activator unit for an autoinjector, comprising a substantially cylindrical housing (3) in which an axially movable pressure pin (4) is guided, said pressure pin being insertable counter to a spring unit and being lockable, when inserted, by means of detent projections (6) of a retaining element (5) that is connected to the pressure pin. The spring unit comprises a first coil spring (1) and at least one second coil spring (2) having a larger diameter than the first coil spring, the second coil spring being coaxial to the first coil spring.

5 Claims, 3 Drawing Sheets

(56) References Cited

U.S. PATENT DOCUMENTS

2013/0197442 A1\* 8/2013 Cowe .................. A61M 5/2033
                                                        604/131
2014/0046259 A1\* 2/2014 Reber ................. A61M 5/2033
                                                        604/136

FOREIGN PATENT DOCUMENTS

| WO | WO 2012/049468 A2 | 4/2012 |
| WO | WO 2012/073035 A1 | 6/2012 |

\* cited by examiner

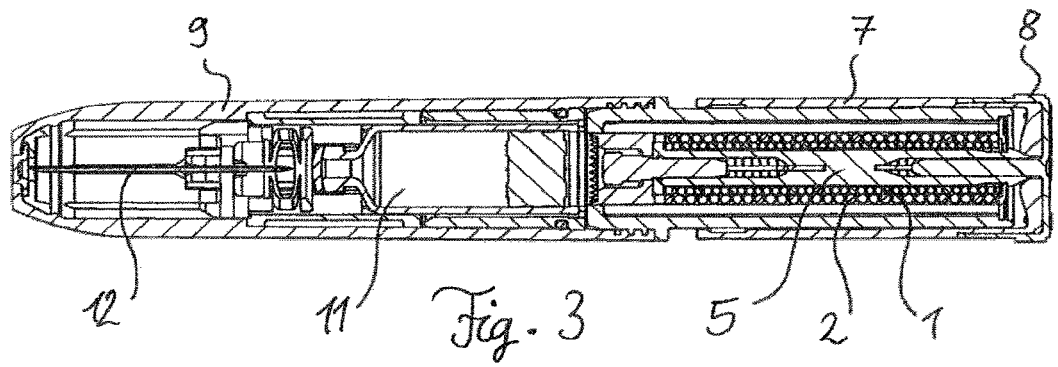
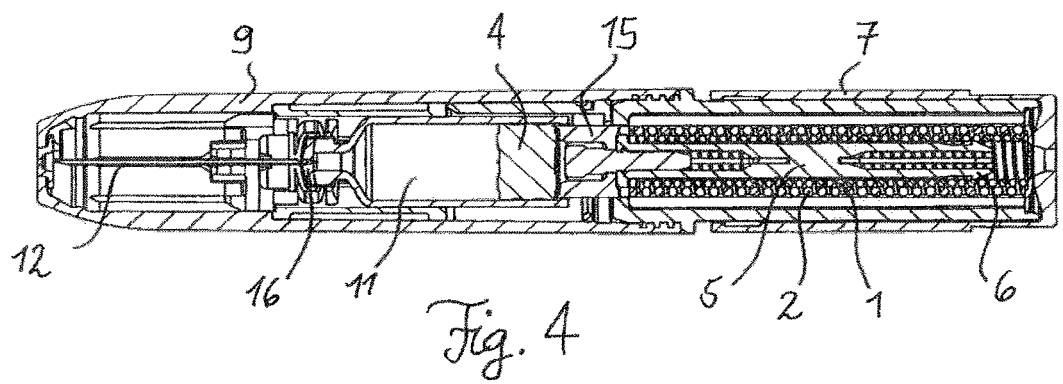
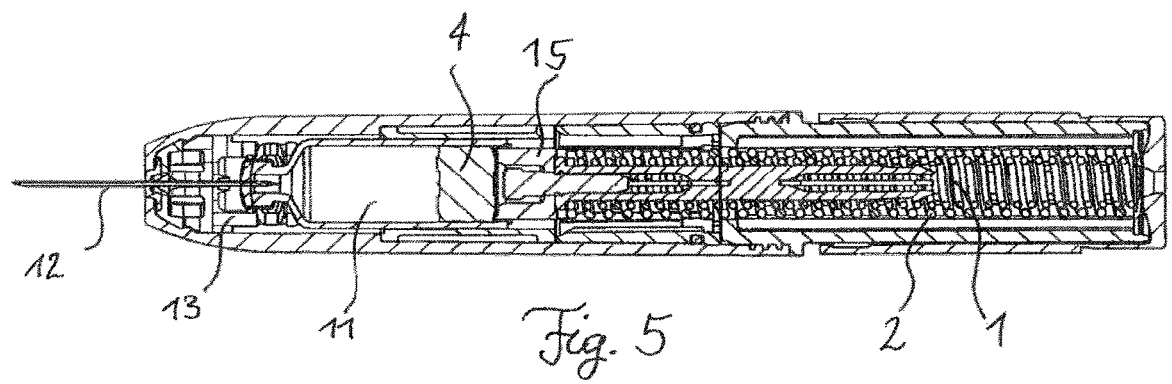
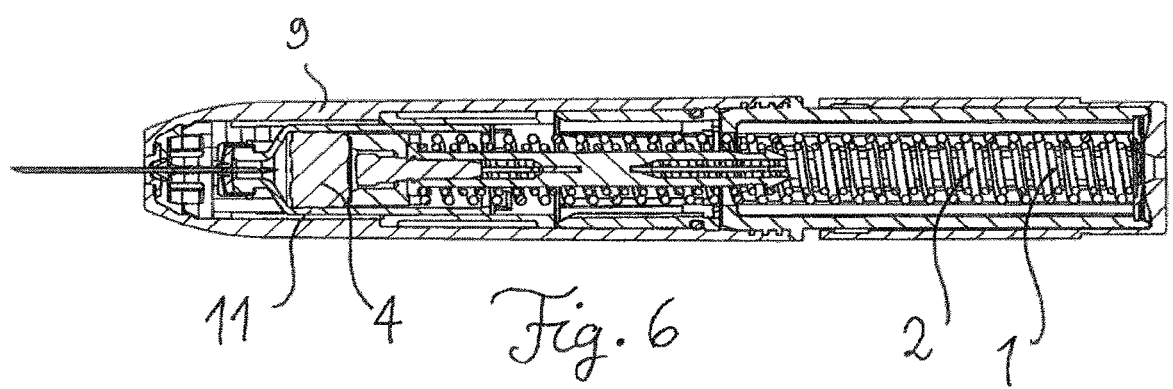

ACTIVATOR FOR AN AUTOINJECTOR

The invention relates to an activator unit for an autoinjector, comprising a substantially cylindrical housing in which an axially movable pressure pin is guided, said pressure pin being insertable counter to a spring unit and being lockable, when inserted, by means of detent projections of a retaining element that is connected to the pressure pin. The invention also relates to an autoinjector comprising the activator unit.

Activators of the type mentioned at the outset are used as components of medical hypodermic syringes that can be operated simply, automatically, and mostly for one-time use. Such a syringe, called an autoinjector, is placed with its distal end on a region of interest of the body of a human and is then triggered by a simple manual action, often in the proximal region of the autoinjector. The terms "proximal" and "distal" refer to the perspective of the person using an autoinjector.

WO 2005/021070 A1 shows a device for automatic injection of injection fluids. Said device also comprises an activator in a cylindrical housing in which a piston rod can be pushed by means of a spring. When the spring is triggered, subsequently pushing the piston rod out towards the distal end of the activator, a cartridge is connected to an injection needle, the needle is pushed out of the device for automatic injection, and the piston rod is pressed into the cartridge such that a liquid drug is injected through the needle. Optionally, the needle may already be connected to the cartridge. The disadvantage of this teaching is that the energy accumulator of the activator consists of a coil spring. As a result, the force that is required to inject the liquid can be applied only at the end of the automatic injection process, that is, when the coil spring is in a nearly relaxed state. The available force is sufficient to press a liquid drug through the cannula. However, it is no longer sufficient to press a viscous drug through the cannula and/or to press the drug through a cannula that has a smaller diameter.

It is the object of the invention to provide an activator as mentioned at the outset which applies greater force when the drug is to be injected. In addition, the activator should not be considerably more complex or costly to produce than prior art activators; it should also be easy and safe to operate as compared with prior art activators and should not have larger outer dimensions. A further object is to make operating an autoinjector more comfortable for the patient.

The activator according to the invention attains this object in that the spring unit comprises a first coil spring and at least one second coil spring having a larger diameter than the first coil spring, the second coil spring being coaxial to the first coil spring. A piston rod that extends from the piston to the proximal end of the activator is no longer provided.

A preferred embodiment of the activator unit is characterized in that the first coil spring and the second coil spring have substantially the same length.

In one embodiment of the invention, the first coil spring and the second coil spring are designed as parts of an integral double spring.

In a further embodiment of the invention, the second coil spring is retained and locked by an element that can be moved by the first coil spring, wherein the locking of the second coil spring can be unlocked when the first coil spring is at an outer release point.

In another embodiment of the invention, the first coil spring is retained and locked by an element that can be moved by the second coil spring, wherein the locking of the first coil spring can be unlocked when the second coil spring is at an outer release point.

In one embodiment of the invention, the activator unit preferably comprises an activator sleeve that can be moved in an axial direction, by which the detent projections can be displaced such that the lock is unlocked and the pressure pin can be moved by the spring unit.

It is further preferred in the embodiment of the device according to the invention that the activator unit comprises a removable safety cap which includes an element that fixes the detent projections in place.

In one embodiment of the invention, the activator unit comprises at its distal end a thread or a bayonet lock by which it can be connected to an injector unit.

In one embodiment of the invention, the pressure pin preferably has on its distal end face mechanical means for breaking a seal.

The invention also relates to an autoinjector that includes an activator unit according to the invention.

In the following, the invention will be explained in more detail with reference to an embodiment shown in the figures. Wherein:

FIGS. 3 to 6 show schematic cross-sectional views of an autoinjector.

Figure 1:
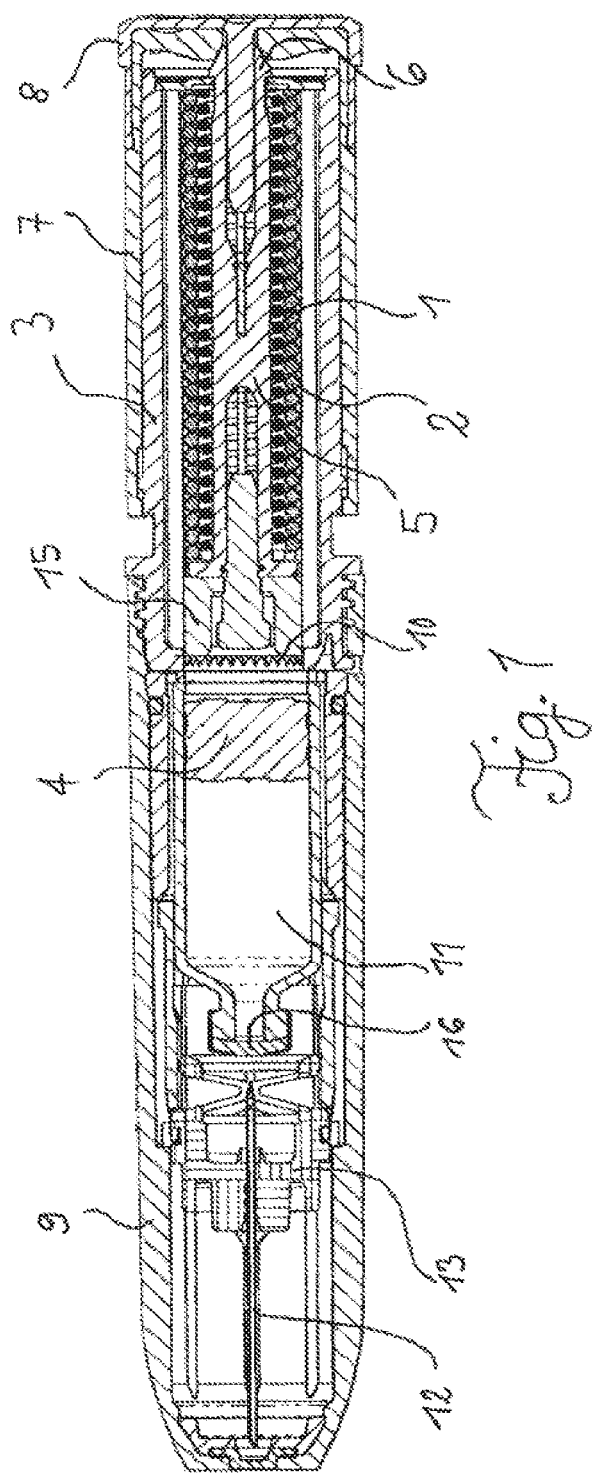
FIG. 1 shows a cross-section of an autoinjector.

According to FIG. 1, an autoinjector comprises an injection unit 9 at its distal end. Located inside said injection unit are a cartridge 11, which contains the drug, and the needle 12. The cartridge 11 is sealed at its distal end by a cartridge seal 16. At its proximal end, the cartridge 11 comprises a pressure pin 4, which can be moved into the cartridge. The needle 12 is held by a needle holder 13. The activator unit is disposed at the proximal end of the autoinjector. It is screwed or otherwise connected to the injection unit 9, and is shown in its secured state in FIG. 1, i.e. a first coil spring 1 and a second coil spring 2 are in the tensioned state between a piston 15 at the distal end and a locking mechanism at the proximal end. To maintain the locked state, a retaining element 5 holds the piston 15 in position by means of detent projections 6. Respective movement of the detent projections 6 along the longitudinal axis of the activator unit is prevented by a safety cap 8 that comprises a central pin which restricts the freedom of movement of the detent projections 6. In addition, an activator sleeve 7 is disposed around the circumference of the housing 3 of the activator unit and can be moved towards the distal end of the activator unit and towards the autoinjector as a whole. In the prior art, it was not possible to accommodate both a first coil spring 1 and a second coil spring 2 in the activator unit. The reason was that the autoinjector as a whole and the activator unit must form a manageable instrument and therefore space inside the activator unit is very limited. Since autoinjectors were previously based on conventional hypodermic syringes, a coil spring was disposed in the interior of the hollow piston rod or in the hollow space within the coil spring. Because the piston rod itself takes up space, there was only enough room for one spring, and therefore a natural ceiling was set for the pressure available to act on the piston. Eliminating the piston rod was not previously considered because this would have given the mechanical elements uncontrollable degrees of freedom, especially in their sequence of movements. According to the invention, however, the long piston rod is removed while at the same time the space that this frees up is taken up by a second coil spring. The resulting surprising effect is that the springs guide each other both in the tensioned locked state and during the injection process, and movement is possible only in the direction of release, i.e. towards the distal end of the activator unit. In this way, the spring force acting on pressure pin 4 and piston 15 can be increased substantially without substantial changes to the external dimensions of the activator unit.

Figure 2:
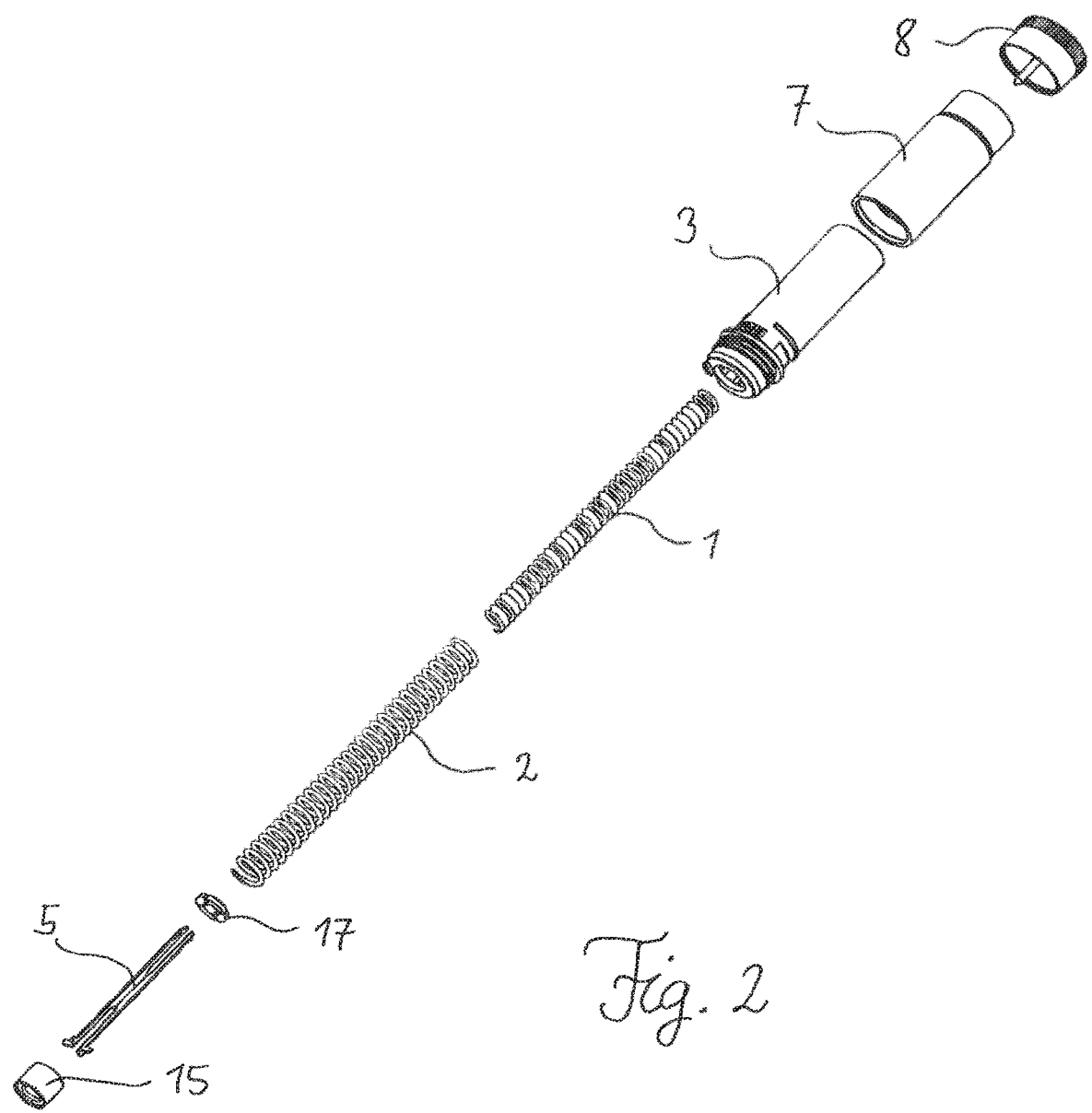
FIG. 2 shows an exploded view of the activator unit.

FIG. 2 shows how the prior art piston, consisting of distal piston end and piston rod, is replaced by only the simple piston 15 shown in FIG. 2. The retaining element 5 is inserted through the first coil spring 1 and the second coil spring 2 and is latched into a proximal opening in the housing 3. Both springs rest on the piston 15 via a spring adapter 17. All that remains is for the activator sleeve 7 and the safety cap 8 to then be placed on the housing 3. The activator unit, which can be produced and stored separately from the injection unit 9, does not need to be sterile. The piston 15 does not apply pressure to the pressure pin 4 of the injection unit 9 until the moment of injection; before that, the piston 15 is locked in place in the activator unit and the pressure pin 5 is seated inside the cartridge 11 in the sterile injection unit 9. To improve its compliance with sterility requirements the injection unit 9 is sealed at its proximal end by a thin film of a suitable material. The seal remains intact even while the activator unit is connected to the injection unit 9 because pressure pin 4 and piston 15 are spaced apart from each other. However, for smooth operation it is advantageous for the piston 15 to have a mechanical means for breaking the seal. This means can consist, for example, in the piston 15 comprising a ring or some other geometric arrangement of teeth on its distal end face, which teeth slit open the film-type seal at the beginning of the injection process.

FIG. 3 shows an autoinjector having the activator unit according to the invention and the injection unit 9 connected thereto in the initial position. The cartridge 11 is sealed and is not yet connected to the needle 12. The first coil spring 1 and the second coil spring 2 are tensioned and are locked by the retaining element 5, which is fixed by the safety cap 8.

FIGS. 4, 5 and 6 illustrate the injection sequence by showing three states of the autoinjector. In FIG. 4, the safety cap 8 has already been removed and the activator sleeve 7 has been moved in the distal direction. At the same time, the distal end of the autoinjector is placed on a body part of a patient, for example (not shown). Moving the activator sleeve 7 has pressed the detent projections 6 of the retaining element 5 toward one another, which releases the lock. The first coil spring 1 and the second coil spring 2 start to relax. This applies pressure to the piston 15, which starts moving into the distal direction. The initial result is that it comes into contact with the pressure pin 4 and starts moving it as well. The injection unit 9 as a whole is now configured such that the pressure pin 4 does not move within the cartridge 11 but carries the cartridge 11 along with it and presses it against the needle 12. The needle punctures the cartridge seal 16 and in this way connects with the cartridge 11 itself.

Once the needle 12 and the cartridge 11 are fully connected, the pressure pin 4, the cartridge 11 along with the drug, and the needle 12 are moved further in the distal direction by the spring pressure applied by both the first coil spring 1 and the second coil spring 2. The needle 12 punctures any seal on the distal end of the injection unit 9, and then the needle 12 penetrates into the patient's body part. Since the needle holder 13 and the cartridge 11 are then at their distal end point and come to a stop inside the injection unit 9, the pressure that is still being applied to the pressure pin 4 by the first coil spring 1 and the second coil spring 2 via the piston 15 then causes the drug to be ejected through the needle 12. In this last step, the high compression force of two springs acting in parallel is unleashed.

FIG. 6 shows the end position of the autoinjector comprising the injection unit 9 and the activator unit according to the invention. Both the first coil spring 1 and the second coil spring 2 have moved the pressure pin 4 to the distal end of the cartridge 11. The drug is now completely ejected.

In the embodiment of the autoinjector comprising the activator unit according to the invention that is shown in the figures, the two springs work at the same time. It is likewise possible for telescopic sleeves known from the prior art to be used to achieve a serial sequence of motions of the first coil spring 1 and the second coil spring 2. In such an embodiment, the first coil spring 1 pushes the cartridge 11 and the needle 12 as well as the second coil spring 2 in the distal direction. During this process, the second coil spring 2 is locked to an element and held therein. This element can be a respective telescopic sleeve. The second coil spring 2 is unlocked shortly before or exactly when the cartridge 11 together with the needle 12 reach their maximum distal point. At that moment, the second coil spring 2 applies the force to eject the drug. It is an advantage of this embodiment that an increased force for ejecting the drug is again available. Conversely, it is also possible for the second coil spring 2 to be released first and to move the first coil spring 1 in a locked state to the distal end, and for the first spring 1 to be released only when cartridge 11 and needle 12 have arrived at the distal end of the autoinjector or are a short distance before it.

Staggered unlocking is necessary particularly with highly viscous active ingredients, which means that an increased spring force is not so much required at the beginning of the motion sequence of the autoinjector, when the cartridge 11 merely has to be connected to the needle 12 and the needle 12 has to puncture the patient's body part, but at the end of the motion sequence, when what is left to do is to push the pressure pin 4 through the cartridge 11.

Another advantage is that the recoil force which occurs when the activator is released and which is perceived as uncomfortable by patients using the device is much lower in the activator according to the invention than in prior art activators.

Various modifications of the embodiments mentioned are conceivable. For example, the first coil spring 1 can be connected to the second coil spring 2 to form an integral double spring. This can prove advantageous in the manufacturing process of the coil spring itself and when assembling the activator unit. The advantage of the increased force resulting from the action of two coil springs on the piston 15 is maintained in this embodiment. It is also conceivable for the activator unit and the injection unit 9 to be configured not as separate and/or connectable to one another via a screwed connection, but as connectable to one another by some other means or produced as a single piece from the start.

The invention claimed is:
1. An autoinjector, comprising:
an injection unit positioned at a distal end of the autoinjector, the injection unit comprising a cartridge including a pressure pin;
an activator unit positioned at a proximal end of the autoinjector, the activator unit comprising a spring unit, the spring unit comprising:
a first coil spring,
a second coil spring coaxial to the first coil spring, wherein the first coil spring and the second coil spring are configured to move together simultaneously toward a distal end of the activator unit, an axially movable piston positioned distal to the spring unit, and a retaining element connected to the piston and positioned within the spring unit, the retaining element having detent projections configured to lock the piston; and a removable safety cap configured to restrict movement of the detent projections.

2. The autoinjector of claim 1, wherein the removable safety cap comprises a central pin configured to restrict movement of the detent projections.

3. The autoinjector of claim 1, wherein the pressure pin is spaced apart from the piston.

4. The autoinjector of claim 1, wherein the pressure pin is configured to move the cartridge in response to pressure applied by the first coil spring and the second coil spring during an injection process.

5. The autoinjector of claim 1, wherein the injection unit comprises a seal at a proximal end of the injection unit, and wherein the piston comprises a mechanical means for breaking the seal.

* * * * *